US010191037B2

(12) United States Patent
Honkanen et al.

(10) Patent No.: US 10,191,037 B2
(45) Date of Patent: Jan. 29, 2019

(54) METHODS OF AND SYSTEMS FOR IMPROVED DETECTION SENSITIVITY OF ASSAYS

(71) Applicant: Aushon Biosystems, Inc., Billerica, MA (US)

(72) Inventors: Peter Honkanen, Concord, MA (US); Scott Douglas, Exeter, RI (US)

(73) Assignee: Aushon Biosystems, Inc., Billerica, MA (US)

( * ) Notice: Subject to any disclaimer, the term of this patent is extended or adjusted under 35 U.S.C. 154(b) by 133 days.

(21) Appl. No.: 14/075,137

(22) Filed: Nov. 8, 2013

(65) Prior Publication Data

US 2014/0134652 A1 May 15, 2014

Related U.S. Application Data

(60) Provisional application No. 61/724,439, filed on Nov. 9, 2012, provisional application No. 61/729,120, filed on Nov. 21, 2012.

(51) Int. Cl.
*G01N 33/53* (2006.01)
*G01N 33/543* (2006.01)
*B01L 3/00* (2006.01)

(52) U.S. Cl.
CPC ...... *G01N 33/5304* (2013.01); *B01L 3/50825* (2013.01); *B01L 3/50853* (2013.01);
(Continued)

(58) Field of Classification Search
None
See application file for complete search history.

(56) References Cited

U.S. PATENT DOCUMENTS 4,707,265 A 11/1987 Barnes, Jr. et al.
4,828,386 A * 5/1989 Matkovich ............. G01N 21/03
356/246

(Continued)

FOREIGN PATENT DOCUMENTS

EP 0976453 A2 2/2000
EP 1122181 A2 8/2001
(Continued)

OTHER PUBLICATIONS

International Search Report and Written Opinion for International App. No. PCT/US13/69255, dated Jan. 31, 2014, 19 pgs.

(Continued)

*Primary Examiner* — Rebecca L Martinez
(74) *Attorney, Agent, or Firm* — Wolf, Greenfield & Sacks, P.C.

(57) ABSTRACT

Systems and methods are disclosed for improved detection sensitivity of assays. The systems include an upper plate that is inserted into a well of testing well, such as a base microtiter plate. For bottom detection, a coating, including polymer coatings or membrane coatings, is applied to an insert portion of the upper plate, and the base plate includes transparent windows. In bottom detection, a detector will image from below the base plate. Alternatively, for top detection, the coating is applied to the well of the base plate, and the upper plate includes transparent windows. In top detection, a detector will image from above the upper plate. Analysis features, including capture antibody features or antigen features, can be printed on the coating surface for forward-phase assays or reverse-phase assays, respectively. Methods for making and using the same are disclosed.

16 Claims, 11 Drawing Sheets

(52) U.S. Cl.
CPC .. *G01N 33/54366* (2013.01); *B01L 2200/025* (2013.01); *B01L 2300/042* (2013.01); *B01L 2300/046* (2013.01); *B01L 2300/0645* (2013.01); *B01L 2300/0654* (2013.01); *B01L 2300/0851* (2013.01)

(56) References Cited

U.S. PATENT DOCUMENTS

| | | | |
|---|---|---|---|
| 5,418,171 | A | 5/1995 | Kimura et al. |
| 7,460,223 | B2 | 12/2008 | Harding |
| 2003/0077207 | A1 | 4/2003 | Tyndorf et al. |
| 2005/0244932 | A1* | 11/2005 | Harding ............... B01L 3/5027 435/91.1 |
| 2007/0154357 | A1 | 7/2007 | Szlosek |
| 2007/0237683 | A1 | 10/2007 | Ho et al. |
| 2009/0305907 | A1 | 12/2009 | Webster et al. |
| 2010/0022416 | A1 | 1/2010 | Flemming et al. |

FOREIGN PATENT DOCUMENTS

| | | |
|---|---|---|
| JP | 2003-522969 A | 7/2003 |
| JP | 2005-528582 A | 9/2005 |
| JP | 2007-178428 A | 7/2007 |
| WO | WO-92/17782 A1 | 10/1992 |
| WO | WO-96/30274 A1 | 10/1996 |
| WO | WO-01/59432 A2 | 8/2001 |
| WO | WO-02/087763 A1 | 11/2002 |
| WO | WO-03/020426 A1 | 3/2003 |
| WO | WO-03/022421 A2 | 3/2003 |
| WO | WO-2011067587 A1 | 6/2011 |

OTHER PUBLICATIONS

Extended European Search Report dated Sep. 12, 2016 in the European Application No. 13853470.6, 16 pages.
Partial Supplementary European Search Report dated Jun. 21, 2016 in the European Application No. 13853470.6, 7 pages.
Office Action for JP App. No. 2015-541945 dated Aug. 21, 2018 and claims pending.

* cited by examiner

METHODS OF AND SYSTEMS FOR IMPROVED DETECTION SENSITIVITY OF ASSAYS

CROSS-REFERENCE TO RELATED APPLICATIONS

This disclosure claims the benefit of priority of U.S. Provisional Application No. 61/724,439, filed Nov. 9, 2012, and U.S. Provisional Application No. 61/729,120, filed Nov. 21, 2012, both of which are incorporated by reference herein in their entireties.

BACKGROUND

Field of Invention

The present invention relates to preparation of assay substrates, and, more specifically, to methods and systems for improving detection sensitivity.

Description of Related Art

An assay substrate is a surface upon which various chemical and/or biological analyses can be performed. Examples of an assay substrate include microarray plates, glass plates, and microtiter plates. A microtiter plate is a flat plate that has multiple "wells" formed in its surface. Each well can be used as a small test tube into which various materials can be placed to perform biochemical analyses. One illustrative use of microtiter plates includes an enzyme-linked immunosorbent assay (ELISA), which is a modern medical diagnostic testing technique.

Generally, in an ELISA, a capture antibody is printed on the bottom of a well in a microtiter plate. The capture antibody has specificity for a particular antigen for which the assay is being performed. A sample to be analyzed is added to the well containing the capture antibody, and the capture antibody "captures" or immobilizes the antigen contained in the sample. A detect antibody is then added to the well, which also binds and/or forms a complex with the antigen. Further materials are then added to the well which cause a detectable signal to be produced by the detect antibody. For example, when light of a specific wavelength is shone upon the well, the antigen/antibody complexes will fluoresce. The amount of antigen in the sample can be inferred based on the magnitude of the fluorescence. In another example, a compound can be added to the well that causes the detect antibody to emit light within a predetermined wavelength (e.g., 400-500 nm). This light can be read by a charge-coupled device (CCD) camera to measure the optical brightness of the emitted light.

Currently, solid-phase 2D multiplexed protein assays use a variety of detection techniques and substrate-surface preparations. Known detection techniques include fluorescence, chemiluminescence, or colorimetric detection. Substrate-surface preparations include a glass substrate with a nitrocellulose surface coating and a plastic substrate with a plasma-treated surface. For example, in one known technique, a nitrocellulose coating is applied to a surface of a glass plate, biological materials (e.g., proteins) are bound to the coating, fluorescence reactions are performed, and the slide is imaged from the printed side.

Current substrate-surface combinations have certain weaknesses. While nitrocellulose-coated glass has excellent binding capacity, it is limited by autofluorescence, that is, emission of natural light by biological structures. The interfering emission from the nitrocellulose coating lowers the accuracy and effectiveness of the fluorescence-based detection techniques. Alternatively, plasma-treated plastic is inexpensive, has consistent surface characteristics, and can be used with a variety of detection techniques. Plasma-treated plastic, however, has low binding capacity.

SUMMARY

The systems and methods disclose biochemical analyses that can be performed with improved sensitivity based on chemiluminescence detection and increased binding capacity. The disadvantages (for example, autofluorescence and low binding capacity) of known substrate-surface preparations can be overcome, or their impact reduced, using the disclosed systems and methods. In the disclosed systems and methods, a detector can detect chemiluminescence without the interference of autofluorescence, or with a reduced impact. In addition, in some embodiments, an insert portion reduces the amount of air between the optical path of illumination and detection, such that optical aberrations caused by the fluid-air interface due to surface tension effects are reduced or eliminated.

In some aspects, a disclosed system includes an assay plate including a well having a geometric shape and a transparent window, the transparent window adapted to being imaged from below a bottom of the well; an upper plate including an insert portion that protrudes into and has a complementary geometric shape to the geometry shape of the well of the assay plate, the insert portion situated above the transparent window; and a coating on the horizontal bottom surface of the insert portion of the upper plate, wherein a gap that is on the order of millimeters forms between the coating surface and the transparent window directly below the gap.

In some embodiments, a system includes an assay plate including a well having a geometric shape; an upper plate including an insert portion that protrudes into and has a complementary geometric shape to the geometric shape of the well of the assay plate, said upper plate having a transparent window that extends through the insert portion, the upper plate adapted to being imaged from above the upper plate; and a coating on a horizontal top surface of the well bottom of the assay plate, wherein a gap that is on the order of millimeters forms between the coating surface and the bottom surface of the insert portion. In some embodiments, an analysis feature is printed on the coating surface. In some embodiments, the coating is a polymer coating. In some embodiments, the coating is a membrane coating. In some embodiments, the gap between the coating surface and the top surface of the transparent window is between about 0.5 mm and about 1 mm.

In some embodiments, the insert portion includes an alignment feature that is adapted to provide an interference fit between the upper plate having an insert portion and the well of the assay plate. In some embodiments, the interference fit is such that the difference between the width of the insert portion and the width of the well is about 200 µm or less. In some embodiments, a fluid fills the gap between the insert portion of the upper plate and the well of the assay plate, wherein an upper level of the fluid is higher than the coating surface. In some embodiments, a fluid fills the gap between the coating surface and the bottom surface of the insert portion, wherein the upper level of the fluid is higher than the bottom surface of the insert portion.

In some embodiments, the system further includes a hole in the upper plate, wherein the hole extends through the insert portion of the upper plate and provides access to the well of the assay plate. In some embodiments, the assay plate is a microtiter plate. In some embodiments, the system further includes a detector that images from below the well through the transparent window of the assay plate. In some embodiments, the system further includes a detector that images from above the upper plate through the transparent window of the upper plate.

In some aspects of the disclosure, an apparatus includes an upper plate including an insert portion that protrudes into and has a complementary geometric shape to the geometric shape of a well of an assay plate, the insert portion being adapted to provide an interference fit between the upper plate having an insert portion and the well of the assay plate, wherein the width of the insert portion differs from the width of the well by about 200 µm or less, and wherein the insert portion that protrudes into the well is adapted to leave a gap between a top surface of the well bottom and the bottom surface of the insert portion. In some embodiments, the insert portion includes an alignment feature that is adapted to provide an interference fit between the upper plate having an insert portion and the well of the assay plate. In some embodiments, the insert portion includes an outer membrane support; an inner membrane support; and a ring membrane attached to the outer and inner membrane supports, wherein the ring membrane leaves a hole in the middle of the insert portion and provides access to the well of the assay plate. In some embodiments, the bottom of the insert portion has a coating, the coating being a polymer coating or a membrane coating. In some embodiments, an analysis feature is printed on the coating.

In other aspects of the disclosure, a method of making a system includes determining a geometric shape of a well of an assay plate, said well of the testing plate having a transparent window adapted to being imaged from below a bottom of the well; molding an upper plate with an insert portion that is adapted to protrude into and has a complementary geometric shape to the geometric shape of the well of the assay plate, the insert portion being adapted to being imaged through the transparent window; and applying a coating on a horizontal bottom surface of the insert portion of the upper plate, wherein a gap on the order of millimeters forms between the coating surface and the transparent window directly below the gap.

In other embodiments, a method of making a system includes determining a geometric shape of a well of an assay plate; molding an upper plate with an insert portion that is adapted to protrude into and has a complementary geometric shape to the geometric shape of the well of the assay plate, the upper plate having a transparent window being adapted to being imaged from above the upper plate; and applying a coating on a horizontal top surface of the well of the assay plate, wherein a gap that is on the order of millimeters forms between the coating surface and the bottom surface of the insert portion. In some embodiments, the methods further include printing an analysis feature on the coating. In some embodiments, the coating is a polymer coating. In some embodiments, the coating is a membrane coating. In some embodiments, the insert portion includes an alignment feature, and further comprising aligning the upper plate having an insert portion and the well of the assay plate to ensure an interference fit. In some embodiments, the insert portion is aligned within the well such that the difference between the width of the insert portion and the width of the well is about 200 µm or less.

In some embodiments, the upper plate includes a hole that extends through the insert portion of the upper plate and provides access to the well of the assay plate. In some embodiments, the assay plate is a microtiter plate. In some embodiments, the insert portion includes an outer membrane support; an inner membrane support; and a ring membrane attached to the outer and inner membrane supports, wherein the ring membrane leaves a hole in the middle of the insert portion and provides access to the well of the assay plate.

In other aspects of the disclosure, a method includes fitting an upper plate to a well of an assay plate, the well having a geometric shape and a transparent window, the transparent window being adapted to being imaged from a bottom of the well; the upper plate including an insert portion that protrudes into and has a complementary geometric shape to the geometric shape of the well, the insert portion situated above the transparent window, wherein a gap on the order of millimeters forms between the bottom surface of the insert portion and the transparent window directly below the gap; wherein a horizontal bottom surface of the insert portion has been coated, and wherein an analysis feature has been printed upon the coating; and conducting a biochemical analysis, including: filling the gap between the bottom surface of the insert portion and the transparent window of the well bottom with a fluid, wherein the upper level of the fluid is higher than the bottom surface of the insert portion; and detecting a signal from below the well of the assay plate through the transparent window of the assay plate.

In some embodiments, the coating is a polymer coating or a membrane coating. In some embodiments, the biochemical analysis is an enzyme-linked immunosorbent assay. In other embodiments, a method includes fitting an upper plate to a well of the assay plate, the well having a geometric shape; the upper plate including an insert portion that protrudes into and has a complementary geometric shape to the geometric shape of the well, said upper plate having a transparent window that extends through the insert portion, said upper plate being disposed such that the well is imaged from above the upper plate; wherein a horizontal top surface of the well bottom of the testing plate has been coated, and wherein an analysis feature has been printed upon the coating; and wherein a gap on the order of millimeters forms between the coating surface and the bottom surface of the insert portion; and conducting a biochemical analysis, including: filling the gap between coating surface and the bottom surface of the insert portion with a fluid, wherein an upper level of the fluid is higher than the bottom surface of the insert portion; and detecting a signal from above the upper plate through the transparent window of the upper plate. In some embodiments, the coating is a polymer coating or a membrane coating. In some embodiments, the biochemical analysis is an enzyme-linked immunosorbent assay.

BRIEF DESCRIPTION OF THE DRAWINGS

FIG. 1A shows a cross-sectional side view of two wells in a microtiter plate.

DETAILED DESCRIPTION

In some aspects, the systems and methods disclose biochemical analyses that can be performed with improved sensitivity based on chemiluminescence detection and increased binding capacity. The disadvantages (for example, autofluorescence and low binding capacity) of known substrate-surface preparations can be overcome, or their impact reduced, using the disclosed systems and methods. In the disclosed systems and methods, a detector can detect chemiluminescence without the interference of autofluorescence, or with a reduced impact. In addition, in some embodiments, using an insert portion reduces the amount of air between the optical path of illumination and detection; thus, optical aberrations caused by the fluid-air interface due to surface tension effects are reduced or eliminated.

Figure 1B:
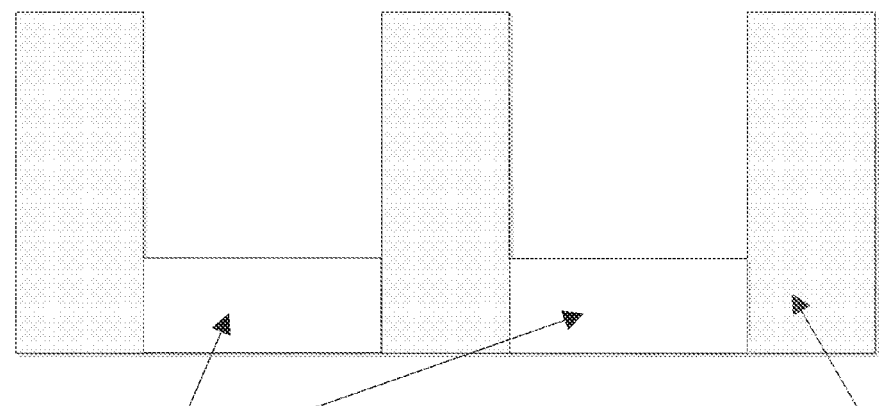
FIG. 1B shows a top view of two wells in a microtiter plate.
Figure 1B:
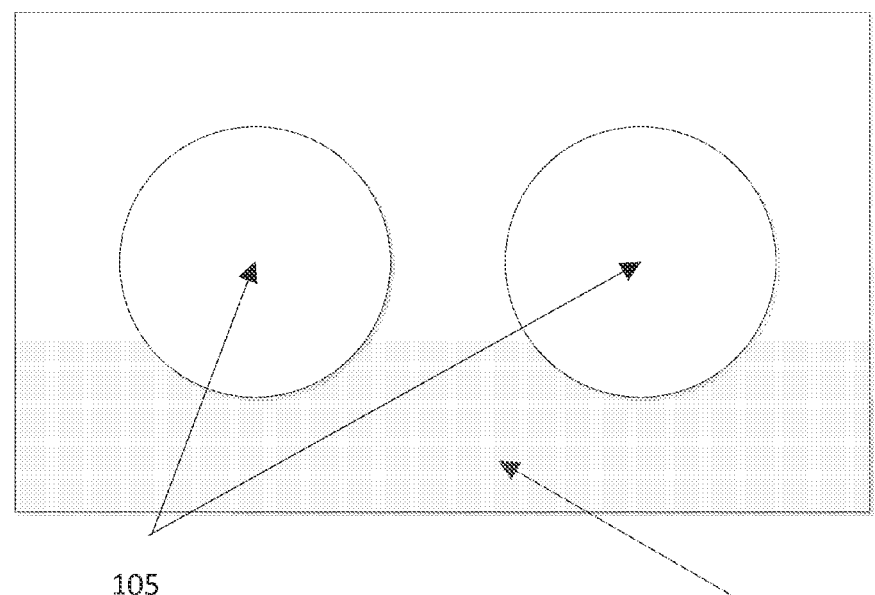

FIG. 1A shows an illustration of a cross-sectional side view of two wells in a microtiter plate 100. In one illustrative implementation, the well substrate 105 is formed of a polystyrene base. Other potential substrate materials include, but are not limited to, nitrocellulose, glass, and other plastic materials. FIG. 1B shows an illustration of a top view of two wells 105 in a microtiter plate 100.

Figure 2:
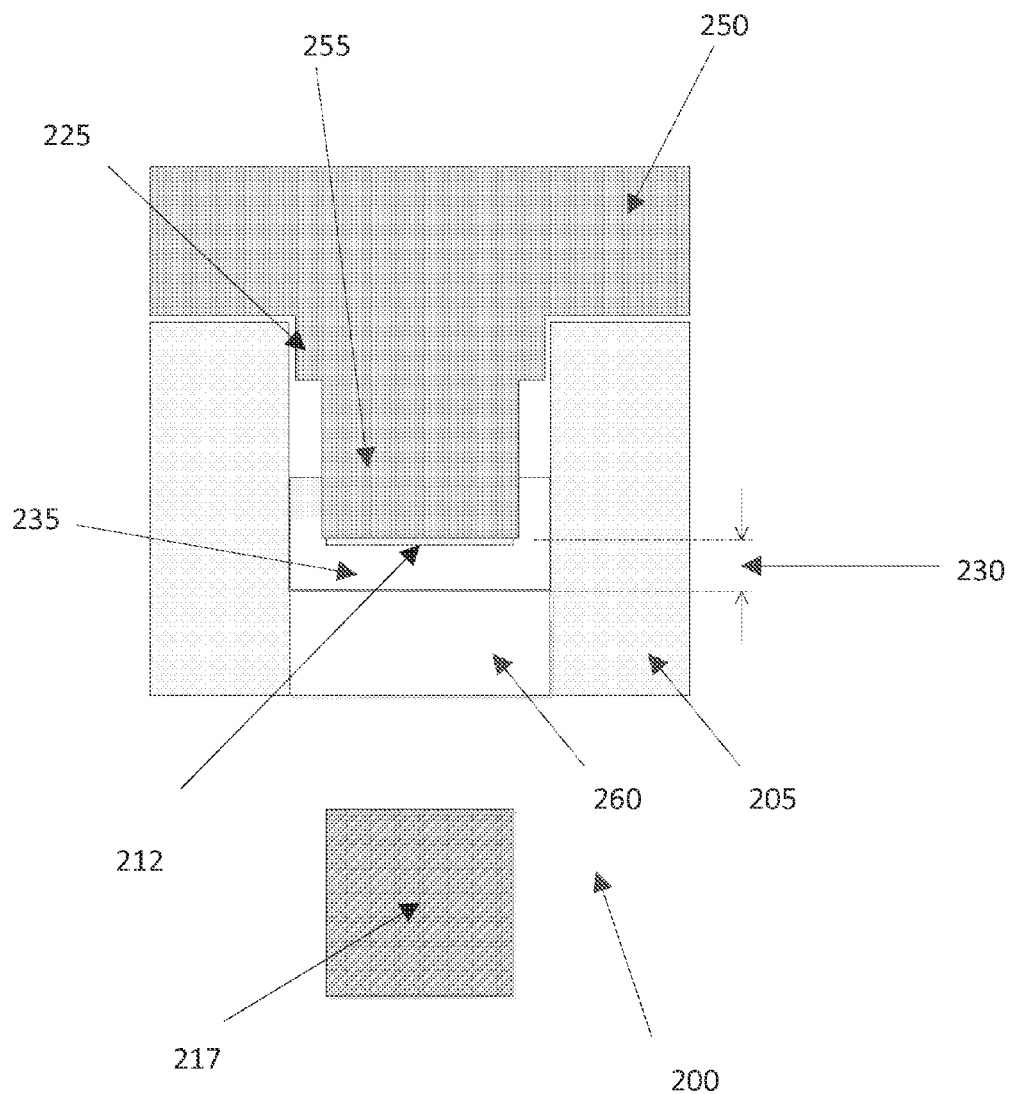
FIG. 2 shows a cross-sectional side view of an insert portion of an upper plate inserted to a well in a microtiter plate for bottom detection in accordance with some embodiments.

FIG. 2 shows a cross-sectional side view 200 of an insert portion 255 of an upper plate 250 inserted to a well 205 of a microtiter plate for bottom detection. As shown in FIG. 2, the upper plate 250 has an insert portion 255 that protrudes into the well 205 of the microtiter plate. The insert portion and testing substrate, for example, a well, possess complementary geometric shapes that fit into one another. The upper plate 250 can be made of materials including, but not limited to, polystyrene and polypropylene. In some embodiments, the insert portion 255 of the upper plate 250 has an alignment feature 225. The alignment feature 225 centers and fixes the insert potion 255 in the well 205 to reduce misalignment during detection. In some embodiment, the alignment feature is sized to provide an interference fit between the upper plate 250 having an insert portion 255 and the well 205 of the microtiter plate. Typically, a molded plate has a dimensional tolerance of about 200 μm, so the alignment feature 225 may be made to fix the insert portion 255 within this tolerance.

In some embodiments, a bottom of the insert portion 255 is coated with nitrocellulose for increased binding capacity. In forward-phase assays, capture antibodies are printed onto the nitrocellulose-coated surface 212. In reverse-phase assays, an antigen (e.g., the protein or material to be analyzed) can be printed onto the nitrocellulose-coated surface 212. Because the nitrocellulose coating renders the bottom of insert portion 255 opaque, detection is carried out from below using a detector 217. Thus, well 205 of the microtiter plate has a transparent window 260.

In some embodiments, there is a gap 235 between the insert portion 255 and the well 205. During an assay, the gap 235 is filled with fluid. The level of the fluid, relative to a substantially horizontal reference plane, is higher than the nitrocellulose-coated surface 212. Thus, the amount of air between the optical path of illumination and detection is reduced or eliminated. Therefore, there is little to no optical aberration caused by surface tension effects. In some embodiments, the distance 230 between the nitrocellulose-coated surface 212 and the top surface of the well bottom 205 is on the order of millimeters. In some embodiments, the distance is between about 0.5 mm and about 1 mm to ensure a proper reaction volume for chemiluminescence detection.

Figure 3:
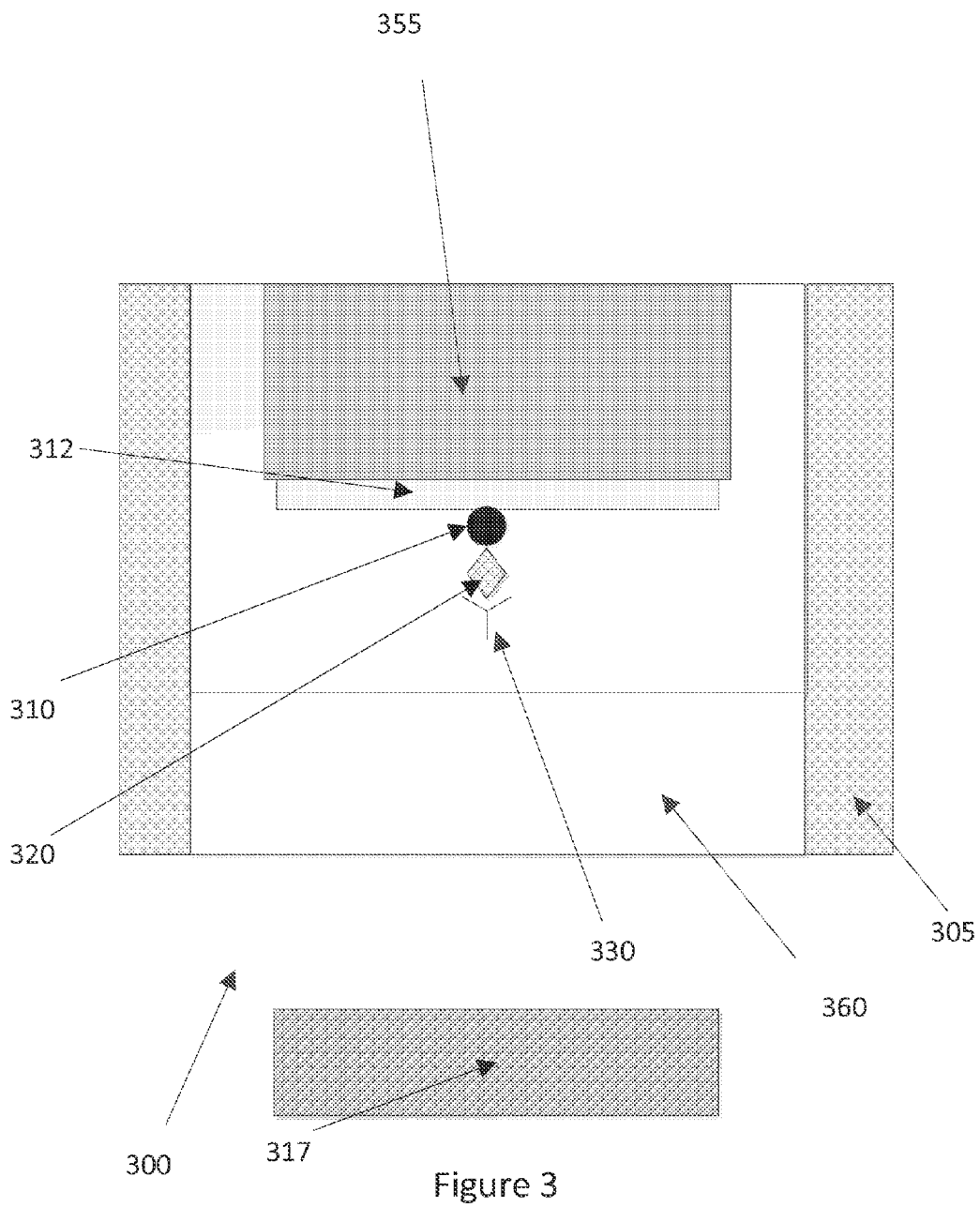
FIG. 3 shows a cross-sectional side view of an insert portion of an upper plate inserted to a well in a microtiter plate during a known method of conducting an ELISA in accordance with some embodiments.

FIG. 3 shows a cross-sectional side view 300 of an insert portion 355 of an upper plate inserted to a well 305 in a microtiter plate during a known method of conducting an ELISA in accordance with some embodiments. Depending on the type of assay, analysis features, including capture antibody features and antigen features, can be printed onto the nitrocellulose coated surface 312 of the insert portion 355. In forward-phase assay, capture antibody or feature 310 are printed onto the nitrocellulose-coated surface 312 of the insert portion 355. During an ELISA, an antigen-containing sample is added to the well. First, the antigen 320 binds to the capture antibody feature 310. Second, the well is washed to remove unbound antigen. Third, enzyme-linked detect antibodies 330 are added. The antibodies 330 bind to the antigen 320. The well is then washed so that unbound antibody-enzyme conjugates are removed. Next, a substance is applied which converts the enzyme into a detectable signal, such as a color, fluorescent, or electrochemical signal. Finally, the absorbency, fluorescence, or electrochemical signal of the well is measured by a detector 317 and compared with a standard to determine the presence and quantity of the sample antigen. A standard can be generated by printing calibration features with a known concentration of antigen in wells that are separate from the wells that receive patient samples.

Embodiments of the invention enable assays with improved sensitivity based on chemiluminescence detection and increased binding capacity. The disadvantages (e.g., autofluorescence and binding capacity) of the known substrate-surface preparation can be overcome using the disclosed systems and methods. A detector can detect chemiluminescence without the interference of autofluorescence. In addition, capture antibodies and antigens are bound by the nitrocellulose coating. Moreover, using an insert portion reduces the optical aberrations caused by the curved fluid-air interface due to surface tension effects.

Figure 4:
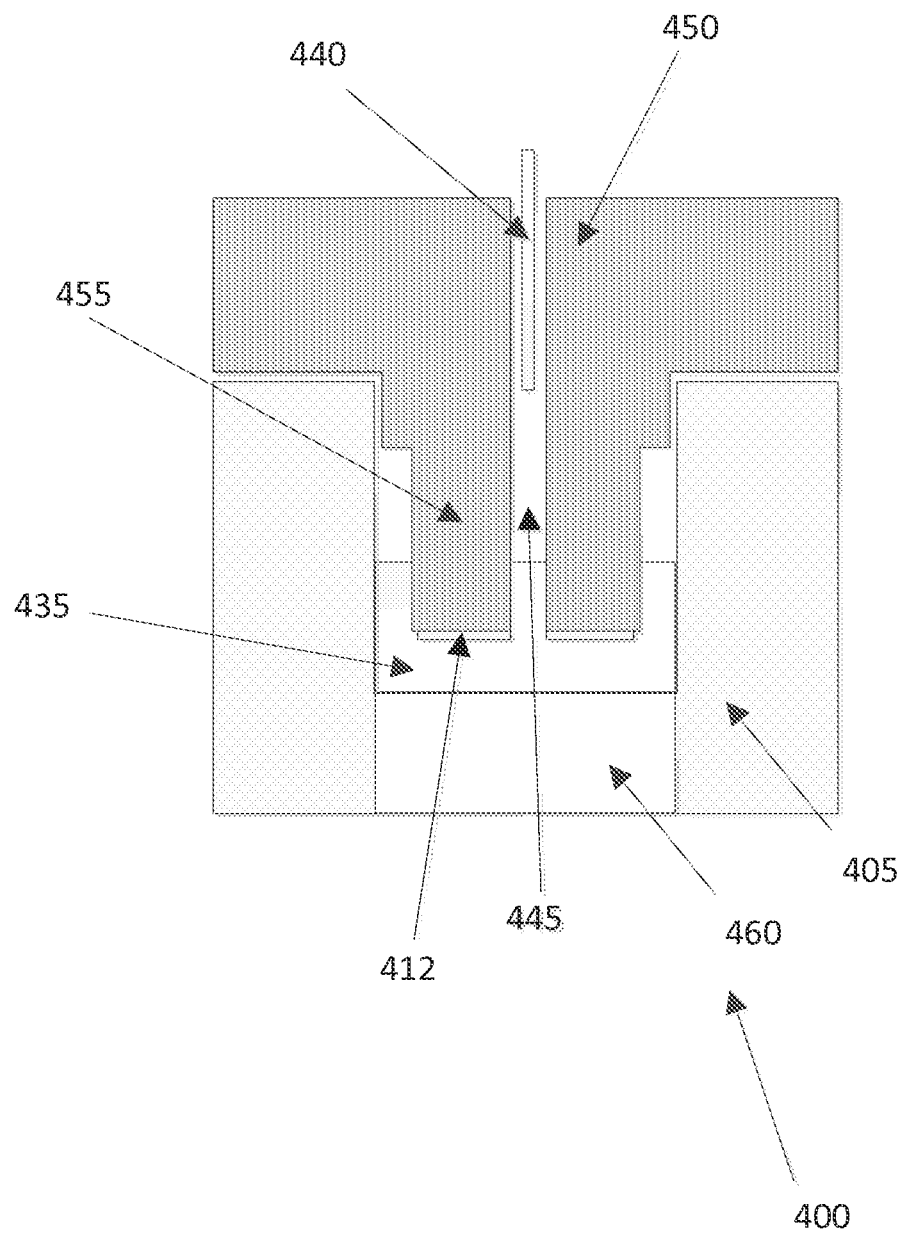
FIG. 4 shows a cross-sectional side view of a hole in an insert portion of an upper plate and a dispensing needle in a hole of the upper plate in accordance with some embodiments.

FIG. 4 shows a cross-sectional side view 400 of an insert portion of an upper plate and a dispensing needle in a hole of the upper plate. In the insert portion 455 of the upper plate 450, there is a hole 445. The hole 445 is designed so that a needle 440 can be inserted in order to introduce fluids into a well 405. The needle 440 may be a commercially available microtiter plate automation tool, including plate washers and fluid dispensers. As a fluid dispenser, the needle 440 may dispense fluid to the gap 435. As a plate washer, the needle 440 may clean the well 405 and the insert portion 455 of the upper plate 450.

Figure 5A:
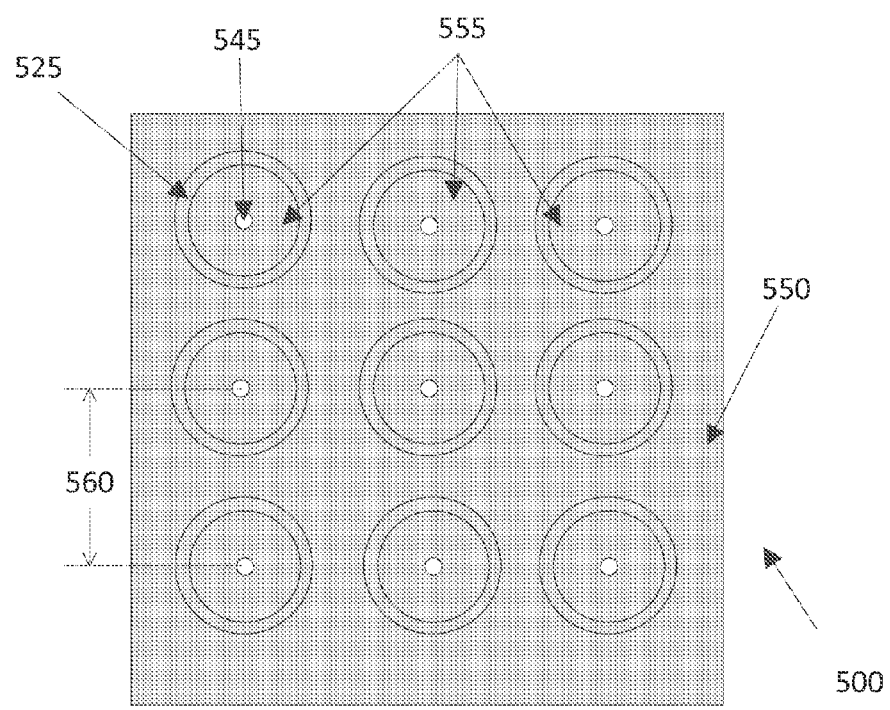
FIG. 5A shows an underside view of insert portions of an upper plate in accordance with some embodiments.
Figure 5B:
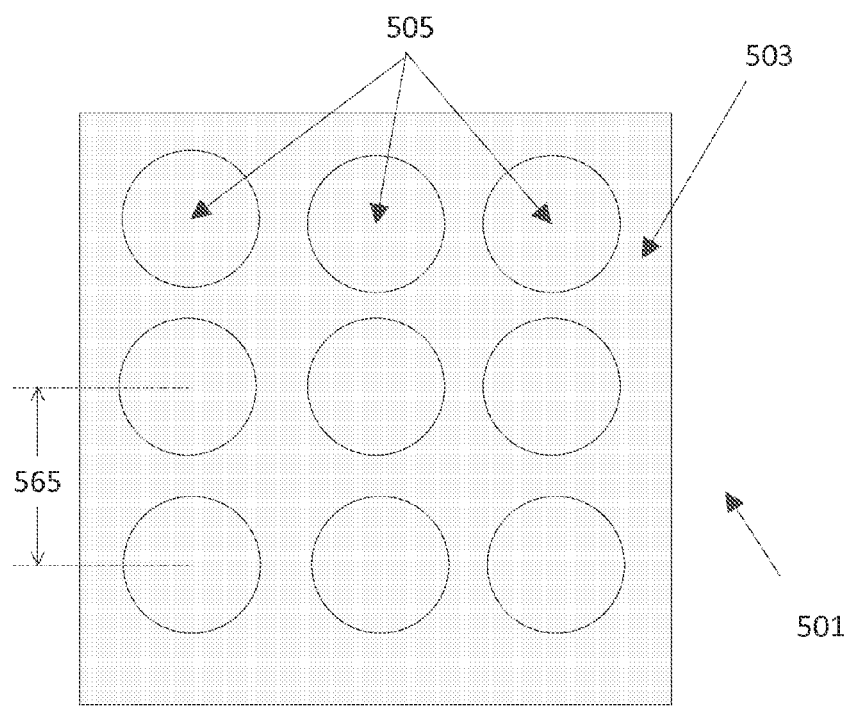
FIG. 5B shows a view of wells of a base plate.

FIG. 5A shows an underside view of the upper plate 550, and FIG. 5B shows a view of a base plate 503. There are multiple insert portions 555 in the upper plate 550. The distance 560 between multiple insert portions 555 can be determined to match the distance 565 between wells 505 of the base microtiter plate 503. Base microtiter plates have a different number and size of wells (or cavities), so the number and size of the insert portions will vary to match the wells of the base plates.

Furthermore, the insert format can be different. For instance, the insert format can be that of standard 25 mm×75 mm (or 1"×3") slide for a 4-cavity microtiter plate for reverse-phase protein assays. Alternatively, the insert format can be circular for a cylindrical-cavity 96-well microtiter plate. The insert format can be made in any configuration to mate with either commercially-available or custom microtiter plate formats. The slide format for reverse phase arrays provides a sufficiently large surface area to print the number of antigen samples, in dilution series, for testing against individual proteins via detection antibodies.

Figure 6:
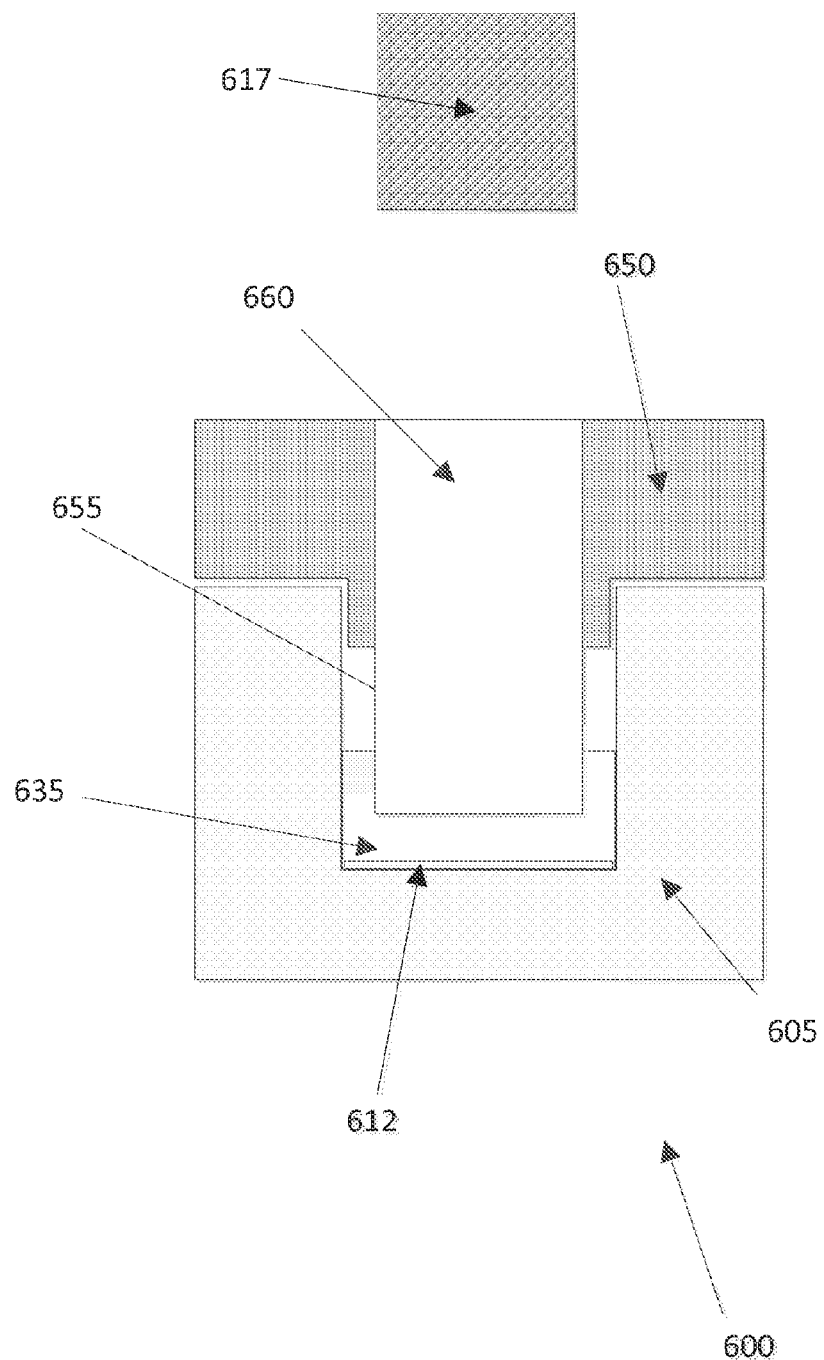
FIG. 6 shows a cross-sectional side view of an insert portion of an upper plate inserted to a well in a microtiter plate for top detection in accordance with some embodiments.

FIG. 6 shows a cross-sectional side view of an insert portion of an upper plate inserted to a well in a microtiter plate for top detection. In these alternative embodiments, a nitrocellulose coating 612 is applied onto a well 605. An upper plate 650 includes a transparent window 660, so that a detector 617 detects photons above the upper plate 650. Similar to the bottom detection embodiments disclosed herein, fluid is filled to a level, relative to a horizontal reference plane, higher than the bottom of an insert portion 655 to reduce optical aberrations due to surface tension effects.

Figure 7:
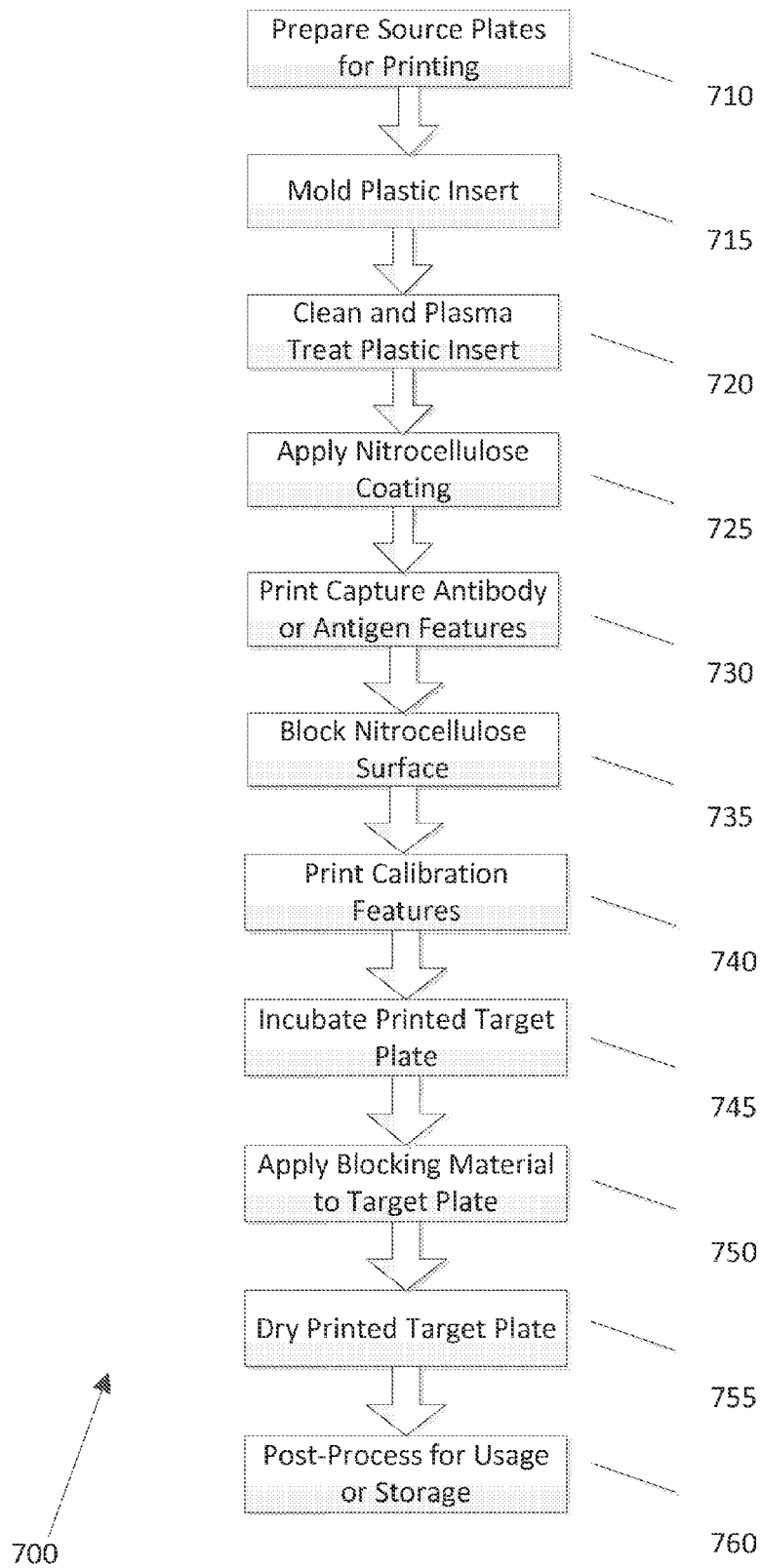
FIG. 7 shows a method of preparing assay substrates to a target plate in accordance with some embodiments.

FIG. 7 shows a method of preparing assay substrates to a target plate in accordance with some embodiments. As used herein, a "target plate" is a plate that is to be prepared (e.g., printed, blocked, and processed for later usage) for a particular set of analyses. For bottom detection, an upper plate is a target plate; for top detection, a base plate is a target plate. A "source plate" is a plate that has a supply of the material to be printed onto a target plate. For example, the wells of a source plate can be filled with various types of antibodies that are to be printed onto target plates. In accordance with a method 700, the source plate is prepared for the printing process (step 710). This can include filling the wells of the source plate with the desired material to be printed onto the target plate.

Next, an upper plate with insert portions is shaped by molding, for example, plastic (step 715). In some embodiments, the upper plate is then cleaned and plasma-treated (step 720). As an option to keep the insert clean, the upper plate is pouched. In some embodiments, a nitrogen-purged, vacuum-packed foil pouch can seal the upper plate. For bottom imaging, a coating, for example, a nitrocellulose coating, is applied to the upper plate (step 725), followed by optional pouching of the upper plate. Alternatively, for top imaging, a coating, for example, a nitrocellulose coating, is applied to the well. Optionally, both plasma treatment and nitrocellulose can be applied to the target plate, or only one of the two can be applied.

For forward-phase assays, the source and target plates are then fit into a printing apparatus (e.g., a 2470 Arrayer available from Aushon Biosystems, Inc. of Billerica, Mass.). Capture antibody features are printed on the nitrocellulose coating of the target plate (step 730). For reverse-phase assays, antigen features are printed on the target plate (step 730). Then, the nitrocellulose surface is blocked (step 735) and dried. The blocking prevents non-selective binding of sample antigens to the base of the well during the ELISA, which would give false readings. The target plate may be pouched until it is used.

Optionally, calibration features can be printed on the test substrate using known methods (including those disclosed in, e.g., U.S. Publication No. 2013/0266969, entitled Method of and System for Printing In-well Calibration Features, filed on Sep. 28, 2012, the contents of which are incorporated by reference in its entirety. (step 740).

The printed target plate is incubated for a period of time (step 745), and a blocking material, which does not react to the capture antibodies or antigen, is applied to the target plate using known methods (step 750). The blocking material adsorbs to the remaining binding surfaces of the plate and binds to antigens of non-specific interaction, thus reducing background signal. The printed target plate is then dried (step 755). In one illustrative implementation, a blocking material solution is applied to the surfaces of the bottoms of a plurality of wells in a microtiter plate via a spraying process, as described in U.S. Publication No. 2012/0135154, entitled Method of and System for Applying Blocking Material to Assay Substrates, filed on Aug. 10, 2011, the contents of which are incorporated by reference in its entirety(step 760).

In other embodiments, the bottom of the insert portion is coated with a membrane rather than a solid coating. A membrane is a film-like structure that acts like a selective barrier, and includes synthetic membranes. Synthetic membranes can be made of organic or inorganic materials, and can include liquid, ceramic, and polymeric membranes. Polymeric membranes include polymers such as cellulose acetate, nitrocellulose, cellulose esters, polysulfone (PS), polyether sulfone (PES), polyacrilonitirile (PAN), polyamide, polyimide, polyethylene (PE), polypropylene (PP), polytetrafluoroethylene (PTFE), polyvinylidene fluoride (PVDF), and polyvinylchloride (PVC). In certain implementations, the membrane is permeable, such that the features printed onto the membrane become incorporated into portions of the membrane structure. The printed features can be detection antibodies for forward phase assays and sample materials for reverse phase assays. Moreover, a permeable membrane enables reactants to flow through the membrane, thereby increasing the assay kinetics and improving wash effectiveness. The permeability of the membrane may vary. In some embodiments, the membrane is a three-dimensional membrane, which allows for high binding capacity per unit area.

Figure 8:
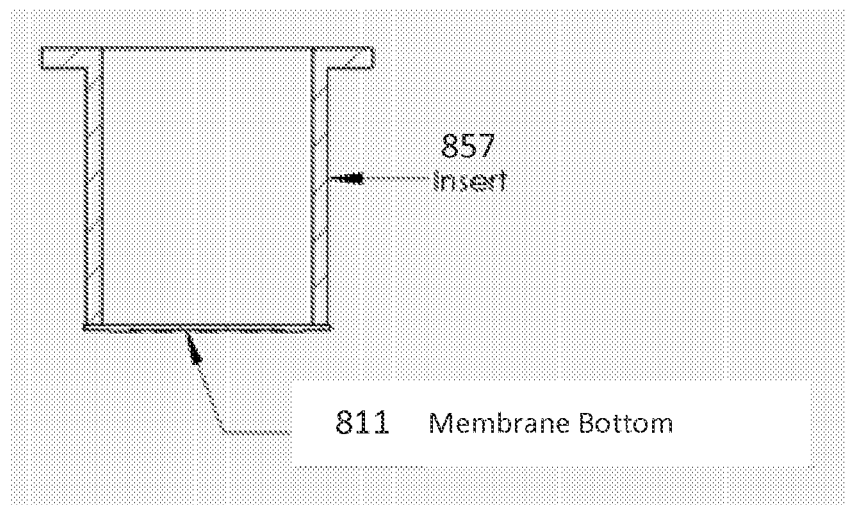
FIG. 8 shows a cross-sectional side view of a full membrane insert of an upper plate in accordance with some embodiments.

FIG. 8 shows a full membrane insert 857. Insert 857 is designed to be disposed in a well of an assay plate in the same manner set forth above. The full membrane insert 857 may be a cylinder that supports a membrane 811; other shapes are within the scope of the invention. In some implementations, the membrane 811 is attached to the insert 857 by adhesive material or is heat welded to the insert 857. In some embodiments, the membrane 811 can be made of nitrocellulose or polyvinylidene fluoride (PVDF). The membrane 811 can also include other materials.

In one illustrative implementation, an adhesive tape is applied to the bottom edges of the cylinder that make up the side walls of the insert 857. The adhesive tape is then removed, leaving the adhesive compound behind on the edge of the side walls. A membrane is then applied to the bottom edge and held in place by the adhesive.

The membrane is unobstructed both above and below the area where antibody or antigen features are printed. The features are printed directly on the membrane, rather than printed on a coated surface. Unlike printing on hard surfaces used in other assay platforms, printing on membranes may be done with light contact between the print head (e.g., print pin) and the membrane or without any contact between the membrane surface and print head or source of feature material.

Figure 9:
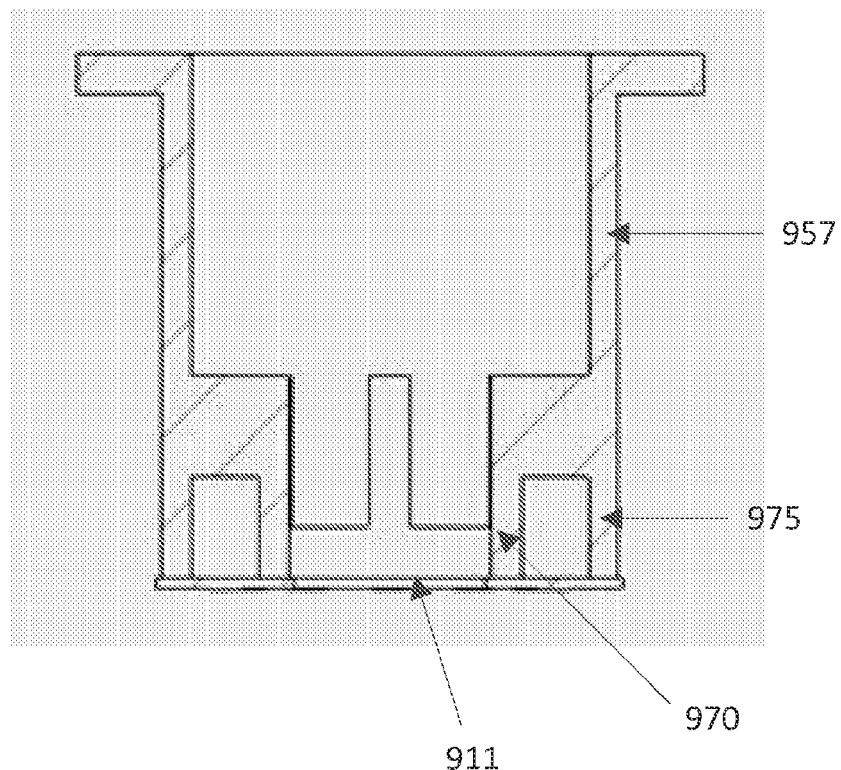
FIG. 9 shows a cross-sectional side view of a ring membrane insert of an upper plate in accordance with some embodiments.

FIG. 9 shows a ring membrane insert 957. The ring membrane insert 957 includes an outer membrane support 975 and an inner membrane support 970. A ring membrane 911 is attached to the two membrane supports. The ring membrane 911 leaves a hole in the middle of the insert 957 to allow access to the bottom of the well when inserted to a well. The hole enables the use of standard assay equipment and techniques by affording access to the well.

Figure 10A:
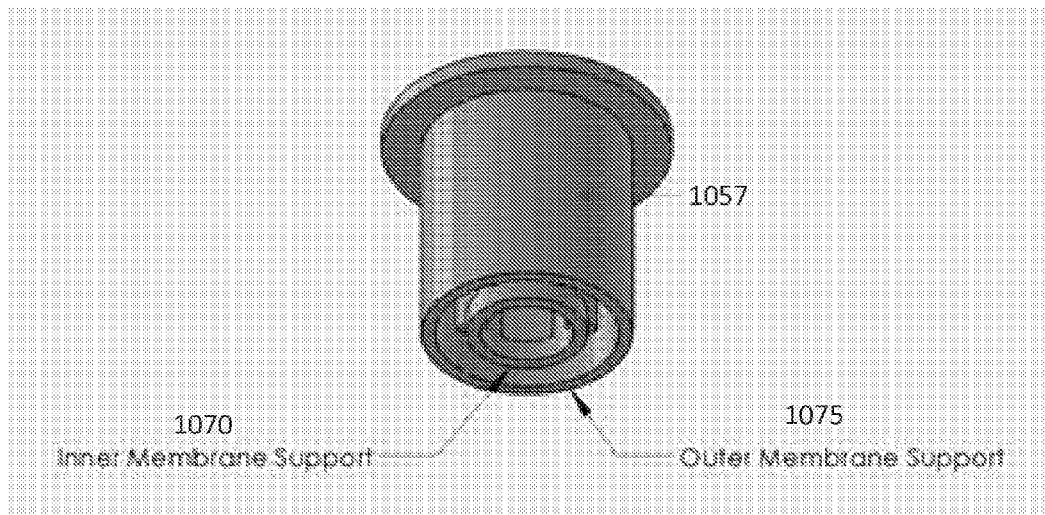
FIG. 10A shows an underside view of an inner membrane support and an outer membrane support of an upper plate in accordance with some embodiments.
Figure 10B:
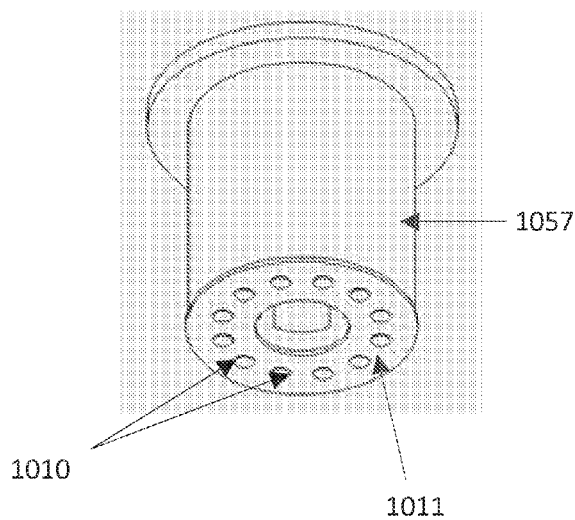
FIG. 10B shows an underside view of a ring membrane attached to a ring membrane support of an upper plate in accordance with some embodiments.

FIG. 10A shows an underside view of a ring membrane insert 1057 without a ring membrane. In this embodiment, both inner and outer supports are cylindrical, supporting a ring membrane. Hollow space exists between the two supports for the free flow of materials. FIG. 10B shows an underside view of the ring membrane insert 1057 with a ring membrane 1011. On the ring membrane 1011, features 1010 are printed.

Figure 11A:
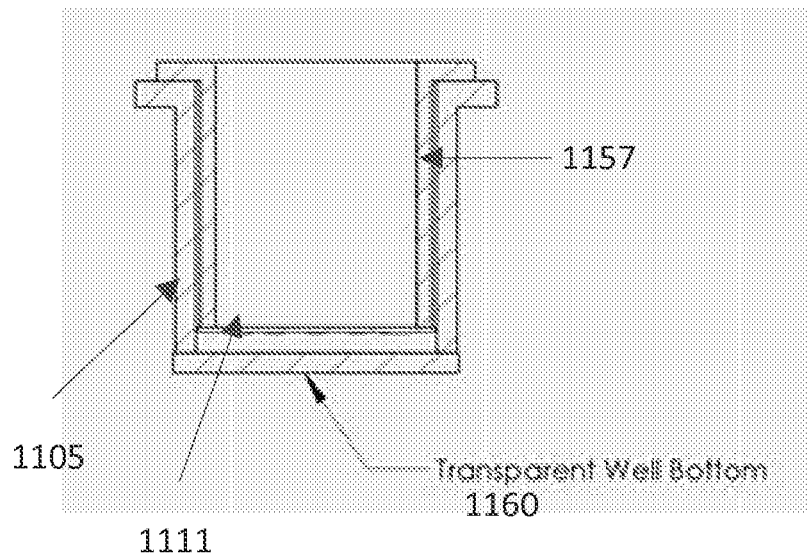
FIG. 11A shows a cross-sectional side view of a full membrane insert of an upper plate inserted to a well in a microtiter plate during a known method of conducting an ELISA in accordance with some embodiments.
Figure 11B:
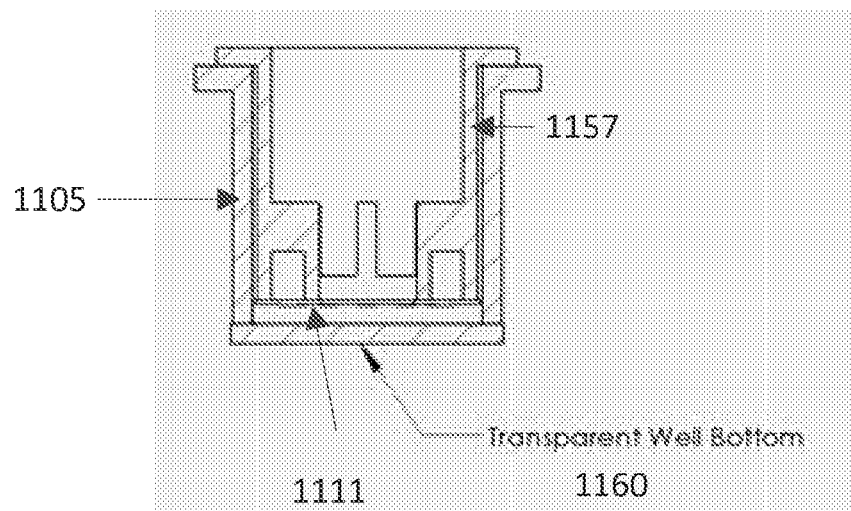
FIG. 11B shows a cross-sectional side view of a ring membrane insert of an upper plate inserted to a well in a microtiter plate during a known method of conducting an ELISA in accordance with some embodiments.

FIG. 11A shows a cross-sectional side view of a full membrane insert of an upper plate inserted to a well in a microtiter plate during a known method of conducting an ELISA in accordance with some embodiments. FIG. 11B shows a cross-sectional side view of a ring membrane insert of an upper plate inserted to a well in a microtiter plate. For the bottom detection, the well 1105 has a transparent window 1160 on the bottom.

During an ELISA, an insert with printed features is inserted to a well and fluid is added to the well for reaction. The fluid can be added to a level, relative to a horizontal reference plane, higher than the membrane. This allows reactants to be carried above the membrane and reduces optical aberration caused by surface tension effects. A detector may detect the chemiluminescence reaction from the bottom through the transparent window.

The specific operational parameters provided above are merely illustrative, and other values are within the scope of the invention.

Kits can be made that incorporate the above devices along with any combination of related equipment or reagents, such as reporter reagents or software for reading and analyzing results of the assay. In some embodiments, the kits include the systems and devices described along with instructions for use.

The embodiments described above can be used to detect the presence of antigens and proteins in a patient, such as a patient having an autoimmune disease, antibodies to viral diseases, antibodies to bacterial diseases, antibodies to allergic reactions, or antibodies to cancers.

The terms and expressions that are employed herein are terms of description and not of limitation. There is no intention in the use of such terms and expressions of excluding the equivalents of the feature shown or described, or portions thereof, it being recognized that various modifications are possible within the scope of the invention as claimed.

What is claimed is:

1. A system comprising:
    an assay plate including a well having a geometric shape and a transparent window below the well;
    an upper plate including an insert portion that protrudes into and has a complementary geometric shape to the geometric shape of the well of the assay plate, the insert portion situated above the transparent window; and
    a coating on a horizontal bottom surface of the insert portion of the upper plate, wherein a gap that is on the order of millimeters forms between the coating surface and a top surface of the transparent window directly below the gap, and
    wherein a plurality of analysis features are printed on the coating on the horizontal bottom surface, and the transparent window is adapted for imaging the analysis feature from below the well.

2. The system of claim 1, wherein at least one of the analysis features is a capture antibody feature or antigen feature printed on the coating surface.

3. The system of claim 1, wherein the coating is a solid coating or a membrane coating.

4. The system of claim 1, wherein the gap between the coating surface and the top surface of the transparent window is between about 0.5 mm and about 1 mm.

5. The system of claim 1, wherein the insert portion includes an alignment feature that is adapted to provide an interference fit between the upper plate having an insert portion and the well of the assay plate.

6. The system of claim 1, wherein a fluid fills the gap between the coating surface and the top surface of the transparent window, wherein an upper level of the fluid is higher than the coating surface.

7. The system of claim 1, further comprising a hole in the upper plate, wherein the hole extends through the insert portion of the upper plate and provides access to the well of the assay plate.

8. The system of claim 1, wherein the assay plate is a microtiter plate.

9. The system of claim 1, further comprising a detector that images from below the well through the transparent window of the assay plate.

10. The system of claim 5, wherein an interference fit is such that the difference between the width of the insert portion and the width of the well is about 200 µm or less.

11. The system of claim 1, wherein the insert portion is cylindrical, and comprises an outer membrane support, an inner membrane support, and a ring membrane attached to the outer and inner membrane supports, wherein the ring membrane is on a horizontal plane that is perpendicular to the vertical axis of the outer and inner membrane supports, and wherein the ring membrane is ring-shaped and leaves a hollow cylindrical space at the cylindrical core of the insert portion.

12. The system of claim 3, wherein the solid coating or membrane coating comprises nitrocellulose or polyvinylidene fluoride.

13. A system comprising:
    an assay plate including a well having a geometric shape and a transparent window below the well;
    an upper plate including an insert portion that protrudes into and has a complementary geometric shape to the geometric shape of the well of the assay plate, the insert portion situated above the transparent window; and
    a coating on a horizontal bottom surface of the insert portion of the upper plate, wherein a gap that is on the order of millimeters forms between the coating surface and a top surface of the transparent window directly below the gap, and wherein an analysis feature and a calibration feature are printed on the coating on the horizontal bottom surface, and the transparent window is adapted for imaging the analysis feature from below the well.

14. A system comprising:

an assay plate including a well having a geometric shape and a transparent window below the well;

an upper plate including an insert portion that protrudes into and has a complementary geometric shape to the geometric shape of the well of the assay plate, the insert portion situated above the transparent window; and a coating on a non-porous horizontal bottom surface of the insert portion of the upper plate, wherein a gap that is on the order of millimeters forms between the coating surface and a top surface of the transparent window directly below the gap, and wherein an analysis feature is printed on the coating on the horizontal bottom surface, and the transparent window is adapted for imaging the analysis feature from below the well.

15. The system of claim 1, wherein at least one of the analysis features is spatially discrete from another analysis feature.

16. The system of claim 1, further comprising a blocking material on the coating on the horizontal bottom surface.

* * * * *